United States Patent [19]

Mackool

[11] Patent Number: 5,084,009

[45] Date of Patent: Jan. 28, 1992

[54] FLUID INFUSION SLEEVE FOR USE DURING EYE SURGERY

[76] Inventor: Richard J. Mackool, 31-27 41st St., Astoria, N.Y. 11103

[21] Appl. No.: 510,431

[22] Filed: Apr. 18, 1990

[51] Int. Cl.⁵ ............................................. A61F 2/32
[52] U.S. Cl. ............................................................ 604/22
[58] Field of Search ............... 128/24 A, 751, 752, 128/753; 604/22, 27, 35, 128, 264, 268; 606/166, 167, 169, 170, 171

[56] References Cited

U.S. PATENT DOCUMENTS

| | | | |
|---|---|---|---|
| 4,515,583 | 5/1985 | Sorich | 604/22 |
| 4,808,154 | 2/1989 | Freeman | 604/22 |
| 4,816,017 | 3/1989 | Hood et al. | 604/22 |
| 4,816,018 | 3/1989 | Parisi | 604/22 |

Primary Examiner—Stephen C. Pellegrino
Assistant Examiner—Steven J. Shumaker
Attorney, Agent, or Firm—Cobrin, Feingertz & Gittes

[57] ABSTRACT

A surgical instrument for removing a cataract from a patient's eye including a hollow vibratable needle surrounded by a hollow infusion sleeve which conforms to the surgical incision and thereby prevents leakage from the incision, and also with means preventing the hollow infusion sleeve from collapsing against the hollow vibratable needle. A second embodiment including a hollow vibratable needle surrounded by two hollow infusion sleeves with conformity of the outer sleeve to the incision and means for preventing the infusion sleeve from collapsing against the hollow vibratable needle.

3 Claims, 2 Drawing Sheets

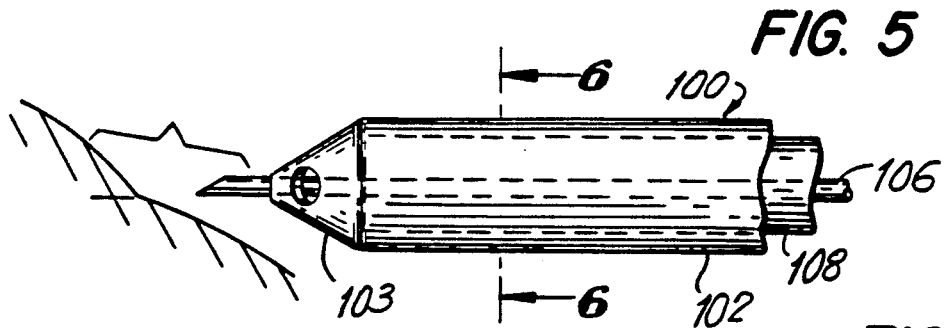
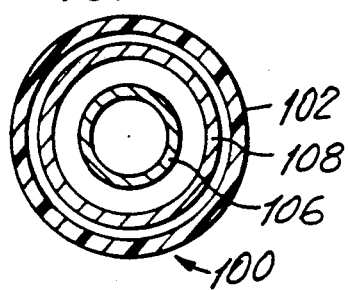
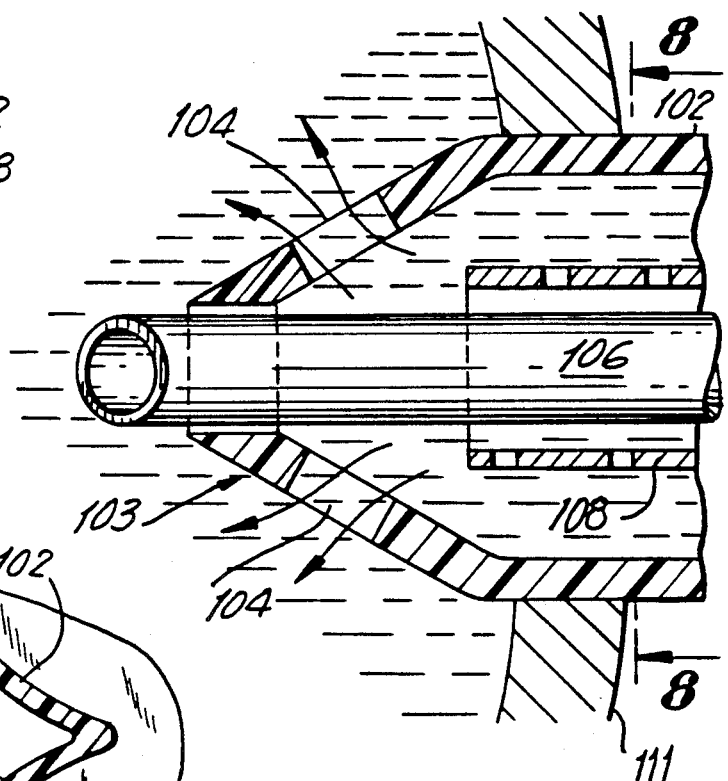
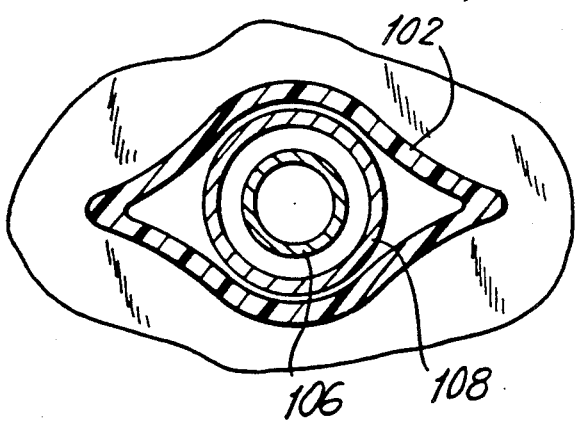
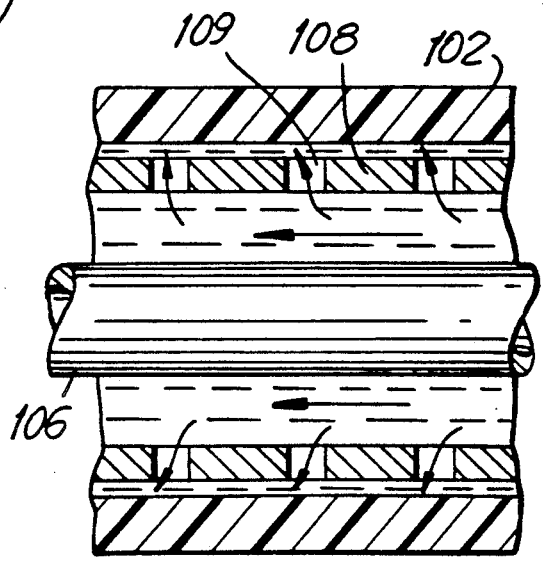

FLUID INFUSION SLEEVE FOR USE DURING EYE SURGERY

BACKGROUND OF THE INVENTION

This invention relates to a surgical instrument for use in eye surgery and particularly cataract eye surgery.

The natural eye in humans contains a lens which focuses on the retina. Due to disease, naturally occurring processes or mutation, the lens may fail to function properly. For example, the lens, by mutation, may have been eliminated from the eye during its formation. Alternatively, the lens may be clouded at birth or become clouded over time. Clouding of a lens is known as a "cataract" which inhibits the transmission of visual information through the lens to the retina.

In the past, the removal of an impaired natural lens required a large incision into the eye at the junction of the cornea and the sclera. As a result, healing time for the incision was substantial. Since the natural lens was removed, eyeglasses or external contact lenses were employed to help restore vision. With the advent of intraocular lenses, incisions initially were still relatively large and healing time remained substantial. The length of the incision required for cataract removal is larger than that required for intraocular lens implantation.

Recently, significant efforts have been made to reduce the size of the incision and such efforts have been successful in substantially reducing the size of the incision for cataract removal to the order of less than 3 mm.

While there has been much success in reducing the size of an incision for cataract surgery, there are still other problems which remain in connection with this surgery.

The method to remove a cataract through a surgical incision in the eye is known as phacoemulsification. Traditionally, this method has involved using a dual chambered instrument consisting of a hollow ultrasonically vibratable metallic needle surrounded by a tubular member. This instrument was inserted through an incision in the eye and the vibratable metallic needle would vibrate at selected frequencies and minute amplitudes fracturing the cataract which was to be removed and replaced by an intraocular lens. While the tip of the vibratable needle serves to engage and fracture the cataract, a suction force is applied through the needle interior to withdraw the fragmented cataract into the needle and out of the eye. During this process, a fluid is infused into the eye through the tubular member which surrounds the vibratable needle. This tubular member is, not surprisingly, known as an infusion sleeve and, in the past, has been made of either a soft silicone material or a rigid composition, in the latter case either metal or teflon.

The importance of infusing a fluid into the eye during cataract surgery cannot be understated. The fluid infusion serves to maintain the eye in an inflated, pressurized condition during cataract removal. These are, however, several factors which increase the difficulties in maintaining an eye during cataract surgery in an inflated, pressurized condition.

One of the most frequent and constant causes of diminished inflation of an eye during cataract surgery is leakage of fluid from the eye. This leakage normally occurs between the egdes of the incision and the exterior surface of the infusion sleeve and can have extreme and adverse consequences to the person being operated on.

One such adverse consequence is that there is a tendency with the loss of fluid for the eye to deflate during the operation which causes the collapse of certain tissues within the eye upon each other or upon the surgical instrument which extends into the eye. The tissues which are most likely to be damaged from the fluid leakage are the cornea, the iris and the lens capsule, all of which surround the cataract. The natural tendency to counteract this fluid leakage is to increase the amount of fluid flow through the eye so that there is proper inflation of the eye. However, this is not a satisfactory solution to the problem of leakage of fluid from the eye because the greater infusion of fluid flow into the eye, the greater the Reynolds number of the fluid such that the flow becomes rapid and even turbulent, causing damage to the cornea and specifically the fragile cells which line the inside of the cornea.

The fragile cells which line the inside of the cornea are known as corneal endothelium and they cannot be regenerated by the eye or, to put it another way, any damage to these cells cannot be repaired by human regeneration. Damage to the corneal endothelium can cause permanent damage to the cornea, resulting in corneal clouding and decreased vision, all of which may require a corneal transplant. In fact, the most common cause of corneal clouding and of corneal transplantation in the United States today are complications from eye surgery during the removal of a cataract and the insertion of an intraocular lens.

It, of course, goes without saying that there would be a tremendous benefit if corneal damage as a result of fluid flow leakage during intraocular surgery could be eliminated.

An early type of infusion sleeve used for intraocular surgery was made of silicone and to this date most of the infusion sleeves used during phacoemulsification are made of silicone or a silicone-type material. However, the use of a silicone-type infusion sleeve presents substantial problems in connection with fluid leakage between the incision edge in the eye and the exterior surface of the silicone infusion sleeve. This results since the incision in the eye must be larger than the silicone infusion sleeve. This is because a silicone infusion sleeve is made from a soft compressible material and cannot be safely used when inserted through an incision in the eye when there is a minimal amount of clearance between the incision and the exterior of the silicone infusion sleeve.

When there is a minimal clearance between the exterior of the silicone infusion sleeve and the incision of the eye, the incision tends to compress the non-rigid silicone sleeve against the vibrating tip which results in relative rubbing movement between the silicone sleeve and the vibrating tip. This relative movement generates undesirable heat as the needle is being vibrated as its relatively high frequencies. The generation of this heat is extremely undesirable inasmuch as it can result in thermal burns and shrinkage of ocular tissue surrounding the silicone compression sleeve. It goes without saying that the burning and shrinkage of ocular tissue is a serious problem and has sight-threatening implications. The rubbing of the infusion sleeve against the vibrating needle also constricts the path for fluid to flow into the eye thereby hampering efforts to keep the eye pressurized and inflated.

In an attempt to reduce the infusion fluid leakage and the deleterious effects that can be caused by undesirable friction generated therefrom, some infusion sleeves have been constructed from rigid non-compressible materials. Generally these materials have consisted of teflon or metallic-based compositions. These rigid, non-compressible infusion sleeves have been relatively successful in solving the problems of constriction of the path for fluid flow between the distal end of the infusion sleeve and the vibrating tip as well as the heat generation and thermal burns associated with malleable infusion sleeves such as the silicone-type sleeve described herein. However, other problems persist with these non-compressible infusion sleeves.

While rigid, non-compressible sleeves are capable of being inserted through smaller incisions which has the inherent advantage of reducing leakage through the clearance between the rigid, non-compressible sleeve and the incision, there is still significant leakage. The primary cause of the persistent leakage between the rigid, non-compressible fluid infusion sleeve and the eye incision is that the cross-section of the rigid, non-compressible sleeve does not match the contour of the eye incision. As a consequence, there are fairly substantial gaps between the rigid, non-compressible sleeve exterior surface and the eye incision. This is because the collagen fiber structure of the cornea resists deformity and thus does not readily assume the shape of the infusion sleeve.

The experience of the applicant, who has performed literally thousands of cataract eye operations, has shown that it is impossible from a practical standpoint to eliminate the problem of leakage during cataract surgery by means of a smaller incision and forcing the infusion sleeve through it. While this may minimize wound leakage, it does not eliminate the problem and in addition causes the instrument to be so tightly held by the deformed incision that there is great difficulty in advancing and withdrawing the instrument through the incision. As will be apparent to those skilled in the art, during cataract surgery the instrument must be advanced and withdrawn many times through the incision as the fractured portions of the cataract are removed from the various locations within the anterior and posterior chambers of the eye.

It is therefore an object of the present invention to provide an improved apparatus for performing cataract surgery.

Still another object of the present invention is to provide an improved surgical instrument for performing cataract surgery which eliminates wound leakage such that it no longer is a practical problem.

Yet a further object of the present invention is to provide a surgical instrument that can be used during cataract surgery for infusing an eye and removing the pieces of a fractured cataract while preventing wound leakage and yet avoid undesirable heat generation heretofore associated with prior art surgical instruments.

A further object of the present invention is to provide an improved surgical instrument that can be used to perform cataract surgery eliminating wound leakage and undesirable heat generation while allowing the vibratable tip to be advanced and withdrawn as is dicated by the necessities of the operation.

The foregoing, as well as other objects, are accomplished by having a surgical instrument which consists of a central vibratable metallic hollow needle surrounded by an infusion sleeve. The infusion sleeve has an ellipsoidal configuration which conforms to the demonstrated configuration of the surgical incision when the incision is opened by the insertion of the instrument. As a consequence of the infusion sleeve matching the configuration of the surgical incision, there is no leakage between the exterior surface of the infusion sleeve and the surgical incision. Still further, the infusion sleeve is normally made of a rigid material such as a metallic material or teflon and thus there is no tendency of the sleeve to collapse and abut against the vibrating metallic needle thereby generating undesirable heat.

As a consequence of the embodiment of the invention just described fluid leakage between the exterior surface of the infusion sleeve and the wound incision is eliminated, providing stable pressure within the eye, eliminating turbulent fluid flow in the eye and correspondingly reducing internal ocular trauma from such turbulent flow. Furthermore, the infusion fluid maintains the ocular tissues in their normal anatomical position preventing collapse thereof either upon themselves or upon the instrument as heretofore occurred.

In a second embodiment of the present invention, an outer silicone infusion sleeve has its distal end tapered so as to be in close proximity to the vibrating needle. Surrounding the vibrating needle is a metallic, non-compressible sleeve which serves the purpose of preventing collapse of the outer silicone infusion sleeve against the vibrating needle. Thus, the outer silicone infusion sleeve will normally assume the shape of the incision (i.e., ellipsoidal) but cannot collapse against the vibrating tip because the metallic infusion prevents this so to preclude the generation of unwanted heat while at the same time eliminating wound leakage.

Other objects of the present invention will be apparent to those having ordinary skill in the art.

BRIEF DESCRIPTION OF THE DRAWINGS

FIG. 5 is a view of an alternate embodiment of the present invention;

FIG. 6 is a sectional view taken substantially along the line 6—6 of FIG. 5;

FIG. 7 illustrates the second embodiment of the present invention as inserted into an eye;

FIG. 8 is a sectional view along the line 8—8 of FIG. 7; and

FIG. 9 illustrates the flow of infusion fluid according to the second embodiment of the present invention.

DESCRIPTION OF THE PREFERRED EMBODIMENTS

Figure 1:
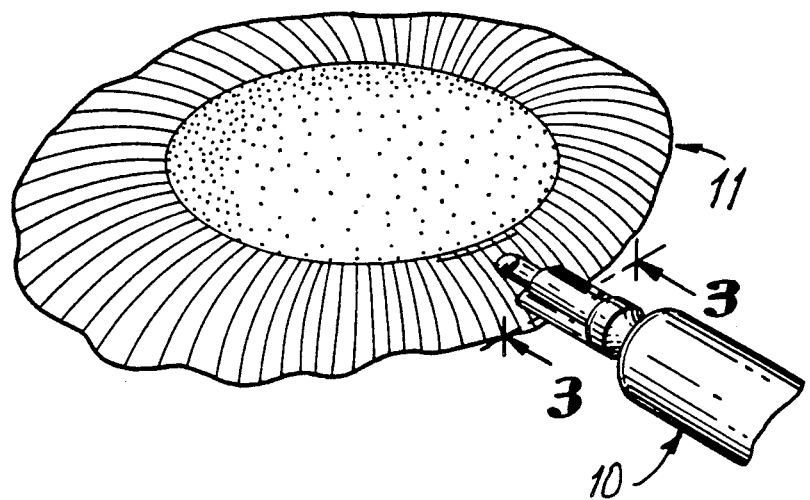
FIG. 1 of the drawings shows a phacoemulsification instrument modified according to the principles of the present invention being inserted into an eye.
Figure 2:
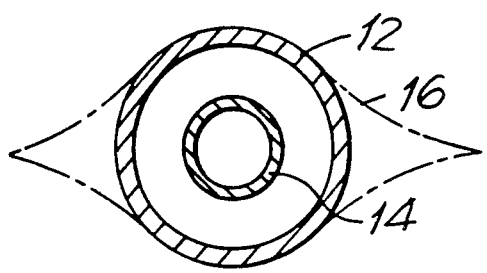
FIG. 2 shows a phacoemulsification instrument according to the prior art and the problems associated therewith.

In FIG. 1 of the drawings a phacoemulsification instrument 10 according to the present invention is shown being inserted into an eye 11 containing a cataract which is to be removed. Instrument 10 is a conventional phacoemulsification instrument and operates as is well known to those of ordinary skill in the art except as modified as described herein. In FIG. 2 of the drawings a conventional phacoemulsification instrument known in the prior art is shown in cross-section and includes a metallic infusion sleeve 12 and a vibrating hollow needle 14. Vibrating needle includes a cataract fracturing tip as is known. Infusion sleeve 12 is circular in cross-section and is concentric with hollow vibratable needle 14. Normally infusion fluid is infused into the eye through sleeve 12 and is sucked out of the eye together with the fractured cataract through the interior of hollow vibrating needle 14.

As can be seen in FIG. 2, infusion sleeve 12 is circular in cross-section and shown in phantom lines is the ellipsodial shape 16 of the wound incision caused by the insertion of a conventional phacoemulsification instrument in the eye of the person who is being operated upon. Because infusion sleeve 12 has a circular cross-section and incision 16 has an ellipsodial cross-section the opposite ends of the incision 16 are not filled by infusion sleeve 12 but are gaps through which infusion fluid leaks from the eye causing all of the problems heretofore discussed.

Figure 3:
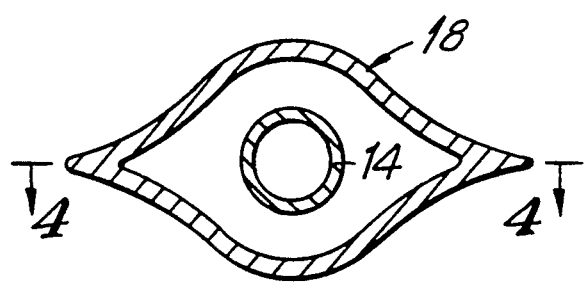
FIG. 3 is a cross-sectional view taken substantially along the line 3—3 of FIG. 1.
Figure 4:
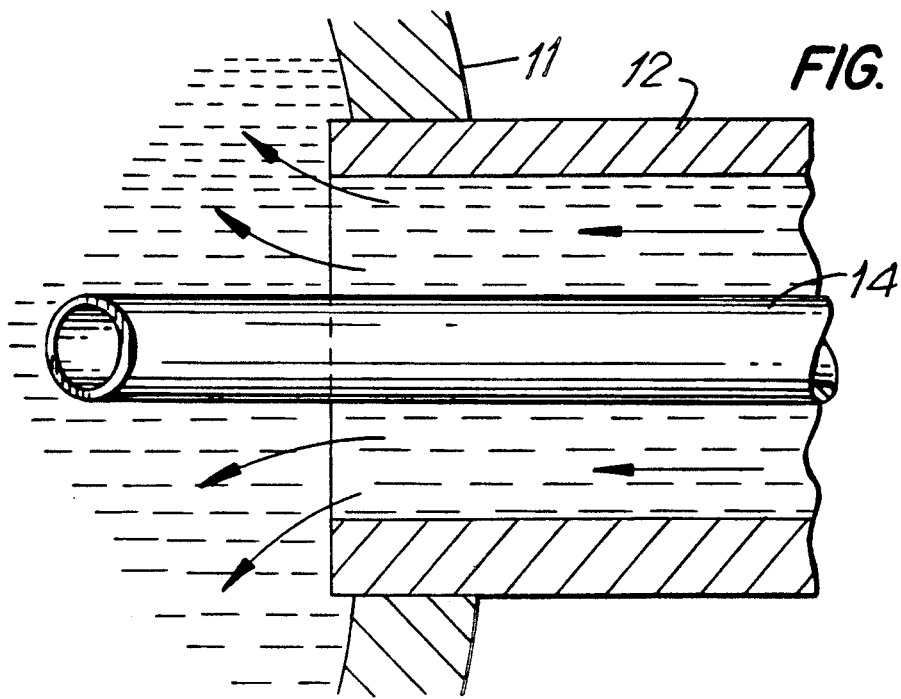
FIG. 4 is a sectional view taken substantially along the line 4—4 of FIG. 3.

In FIG. 3 of the drawings, the cross-section of a phacoemulsification instrument according to the present invention is shown. The phacoemulsification instrument in FIG. 3 is identical and operates in the same fashion as prior art phacoemulsification systems, except that the infusion sleeve 18 is of a ellipsodial cross-section. This change in configuration of the infusion sleeve over what has been practiced in the prior art is of great importance because now the infusion sleeve fills the incision which is formed in the person's eye since it has an ellipsoidal cross-section. As a consequence, there is no wound leakage, pressure in the eye is maintained and the problems associated with wound leakage are avoided. The surgical instrument is used as shown in FIG. 4.

The infusion sleeve 18 of the present invention is made of a metallic, rigid, non-compressible material or, alternatively, of teflon. The infusion sleeve 18 of the present invention provides stable pressure in the eye since it eliminates would leakage, eliminates turbulent flow in the eye and correspondingly eliminates internal ocular trauma from such turbulent flow. Furthermore, because there is no wound leakage, the ocular tissues are maintained in their normal anatomical position and do not collapse upon each other or upon the instrument as can otherwise occur as a result of excessive wound leakage and lowered intraocular pressure.

In FIGS. 5-9 an alternate embodiment of the present invention is shown. Embodiment 100 includes an exterior silicone infusion sleeve 102 which is circular in cross-section and has a tapered distal end 103. Adjacent end 103 are discharge ports 104. Concentric with infusion sleeve 102 is a hollow vibrating needle which is identified by the reference numeral 106 and is conventional. Surrounding hollow vibrating needle 106 is a metallic, non-compressible sleeve 108 that does not portion of infusion sleeve 102. Sleeve 108 may include radial discharge ports 109. Infusion sleeve 102 and sleeve 108 are both concentric about vibrating needle 106. The cross-section of infusion sleeve 102, while circular (FIG. 6), can be snug fitted through a wound incision and will assume the ellipsoidal configuration of the incision inasmuch as silicone is a readily deformable material and thus can assume this configuration.

Heretofore, in the prior art when efforts were made to snugly extend a silicone infusion sleeve through an incision the sleeve would collapse to some extent and abut the vibrating needle causing severe fluid flow constriction as well as undesirable heat generation. To the extent the silicone sleeve tends to collapse, it cannot abut against the vibrating needle because it will first abut metallic sleeve 108 which will prevent this undesirable contact.

The infusion sleeve, while normally circular, when inserted into eye 111 assumes the ellipsoidal shape of the eye (FIG. 8).

In using the embodiment of the invention shown in FIGS. 5-9, attention is directed to FIG. 9 which shows infusion fluid being directed through the interior of sleeve 108 and through discharge ports 109 thereof and then to the interior of silicone infusion sleeve 102 and ultimately from there through discharge ports 104 into the interior of the eye. This is one mechanism by which infusion fluid may thus pass between the two infusion sleeves and thereby gain access to the eye. Another mechanism would be the simple delivery of infusion fluid between the two sleeves with such infusion fluid entering the space between the two sleeves at the origin of said sleeves.

In the embodiment of the invention just described, it is noteworthy that the tapered end of the silicone infusion sleeve 102 will not abut against the vibrating needle 106 since this portion of the instrument is never maintained within the incision during periods of vibration of needle 106. This tapering accomplishes the purpose of radial discharge of fluid through ports 104, thereby avoiding the direction of fluid parallel to the needle 106, which would oppose the fractured cataract being drawn into the interior of the hollow vibratable needle 106. Furthermore, the metallic sleeve 108 need not taper inward toward needle 106, since the tapering of the silicone infusion sleeve 102 accomplishes the correct direction of the fluid. The non-tapering metallic infusion sleeve 108 therefore has a substantially greater tolerance surrounding the vibratable needle 106 as compared to current tapered metallic infusion sleeves, which has important practical ramifications. Current tapering metallic infusion sleeves have strict concentricity requirements which can be accomplished by the instrument manufacturer with special equipment. This absolute concentricity is mandatory since contact of the metallic infusion sleeve and the vibrating needle must always be avoided since such contact would result in the creation of heat and also the dispersion of metallic particles within the eye. However, since vibrating titanium needles gradually wear and require replacement, this concentricity requirement results in the need for the instrument to be returned to the manufacturer for needle replacement. With the present invention, the clearance between the non-tapered portion of sleeve 108 and hollow vibrating needle 106 is large enough to permit the vibrating needle to be exchanged by the surgeon or nurse without returning the instrument to the manufacturer.

It can thus be seen that the instruments of the present invention eliminate wound leakage while enabling a cataract to be safely and properly removed by a surgeon. The elimination of wound leakage, together with the elimination of undesired heat generation while maintaining the eye at the proper inflated pressure represents a significant advance in the never-ending search to minimize potential harm to patients during cataract surgery.

Having described the specific preferred embodiments of the invention with reference to the accompanying drawings, it will be appreciated that the present invention is not limited to those precise embodiments, and that various changes and modifications may be effected therein by one of ordinary skill in the art without departing from the spirit of the invention as defined by the appended claims.

What is claimed is:

1. A surgical instrument for removing a cataract through an incision in a patient's eye, comprising a hollow, compressible infusion sleeve; said hollow, compressible infusion sleeve including a tapered, ported distal end portion designed to be located within a patient's eye during cataract removal and having an extreme end portion; said hollow, compressible, infusion sleeve further including a second cylindrical portion configured and designed to extend into a patient's eye; said second cylindrical portion intersecting with and extending away from said tapered, ported distal end portion; a hollow vibratable needle which extends into a patient's eye during the removal of a cataract; said hollow, compressible infusion sleeve second cylindrical portion and said tapered, ported distal end portion surrounding said hollow, vibratable needle with there being a space between the extreme end portion of said tapered, ported distal end portion and the hollow, vibratable needle; a rigid, hollow, non-compressible sleeve surrounding a portion of said hollow, vibratable needle with said rigid, hollow, non-compressible sleeve having a larger diameter than said hollow, vibratable needle, thereby defining a path of fluid between said hollow, vibratable needle and said rigid, hollow, non-compressible sleeve; said rigid, hollow, non-compressible sleeve being surrounded by said hollow, compressible infusion sleeve second cylindrical portion and a portion of said tapered, ported distal end portion of said hollow, compressible infusion sleeve, whereby said rigid, hollow, non-compressible sleeve prevents the hollow, compressible infusion sleeve from collapsing against said hollow, vibratable needle.

2. A surgical instrument for removing a cataract according to claim 1, wherein said rigid, hollow, non-compressible sleeve includes radial ports.

3. A surgical instrument for removing a cataract according to claim 1, wherein said compressible infusion sleeve distal end portion includes discharge port means for directing fluid at an angle with respect to the axis of the hollow, vibratable needle and away therefrom.

* * * * *